United States Patent [19]

Paterson

[11] Patent Number: 5,116,325

[45] Date of Patent: May 26, 1992

[54] NEEDLE ASSEMBLY

[76] Inventor: Donald W. Paterson, 8 Chamier Road, Moument Heights, Kimberley, Cape Province, South Africa

[21] Appl. No.: 708,999

[22] Filed: May 31, 1991

[30] Foreign Application Priority Data

Jun. 6, 1990 [ZA] South Africa .................. 90/4357
Dec. 4, 1990 [ZA] South Africa .................. 90/9742

[51] Int. Cl.⁵ ............................................. A61M 5/32
[52] U.S. Cl. ................................... 604/192; 604/263
[58] Field of Search ................... 604/192, 187, 263

[56] References Cited

U.S. PATENT DOCUMENTS

| | | | |
|---|---|---|---|
| 4,659,330 | 4/1987 | Nelson et al. | 604/192 |
| 4,747,836 | 5/1988 | Luther | 604/198 |
| 4,838,871 | 6/1989 | Luther | 604/263 X |
| 4,872,552 | 10/1989 | Unger | 206/365 |
| 4,886,503 | 12/1989 | Miller | 604/192 |
| 4,909,791 | 3/1990 | Norelli | 604/192 |

FOREIGN PATENT DOCUMENTS

| | | |
|---|---|---|
| 0369619 | 5/1990 | European Pat. Off. . |
| 9001348 | 2/1990 | PCT Int'l Appl. . |
| 691420 | 2/1969 | South Africa . |
| 694864 | 7/1969 | South Africa . |
| 725928 | 8/1972 | South Africa . |
| 733987 | 6/1973 | South Africa . |
| 746318 | 10/1974 | South Africa . |
| 773701 | 6/1977 | South Africa . |
| 767239 | 12/1977 | South Africa . |
| 881559 | 3/1988 | South Africa . |
| 890571 | 1/1989 | South Africa . |
| 890787 | 2/1989 | South Africa . |
| 891309 | 2/1989 | South Africa . |
| 895951 | 8/1989 | South Africa . |

Primary Examiner—John D. Yasko
Attorney, Agent, or Firm—Ladas & Parry

[57] ABSTRACT

A needle assembly 10 comprises a needle device 11 having a needle base 14 and a hollow needle 12, having a free end 13 which is sharpened or pointed, protruding from the base, with a passageway 15 extending along the needle. An opening 17 to the passageway is provided in proximity to the sharpened end or point of the needle. A needle guard comprising an elongate protective sheath 20 provided around the needle base and the needle such that the sharpened end of the needle is protected by the sheath. An elongate opening 24 extends along the sheath and the needle can pass through it. First hinge components 30 are located on the sheath. Second hinge components 16 are provided on the base. The first and second hinge components co-operate with each other such that the needle guard is pivotal from a primary position in which the sharpened needle end or point is protected by the sheath, to a secondary position in which the needle point is exposed for use.

7 Claims, 4 Drawing Sheets

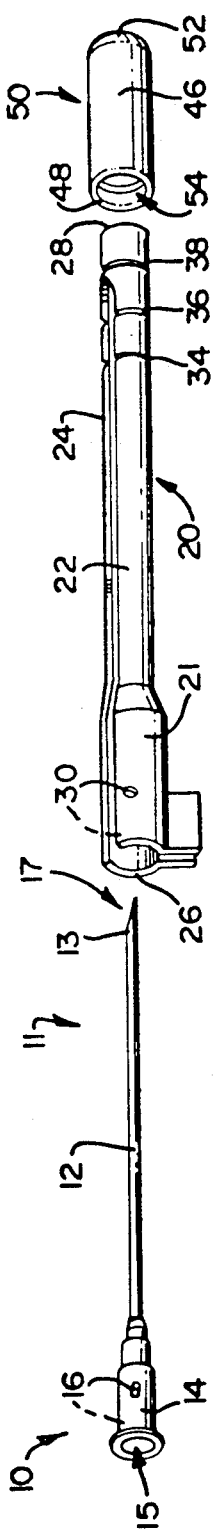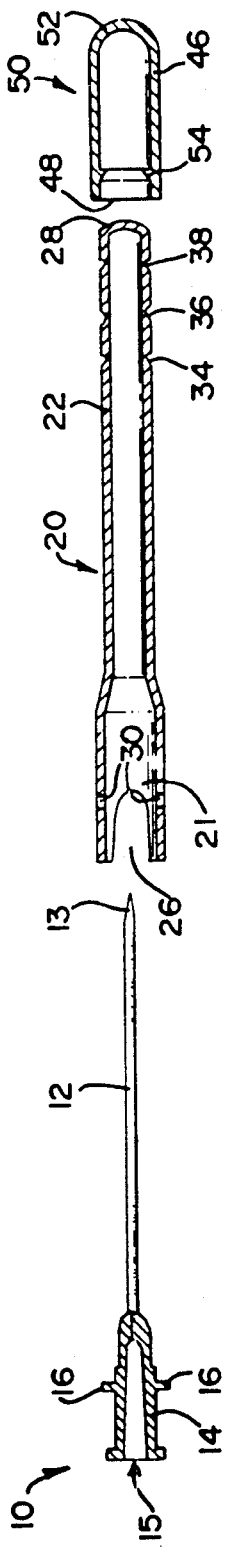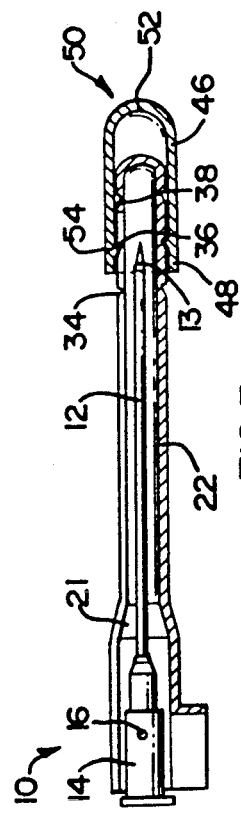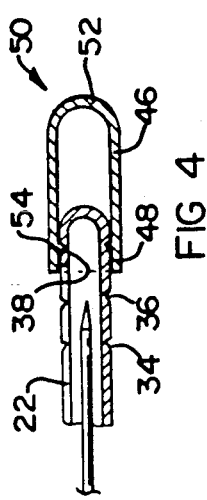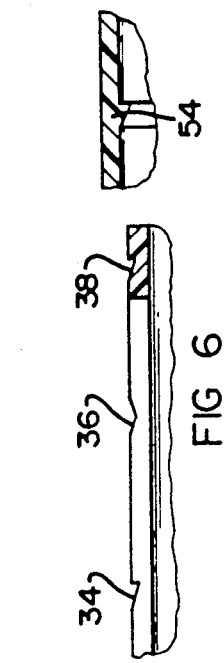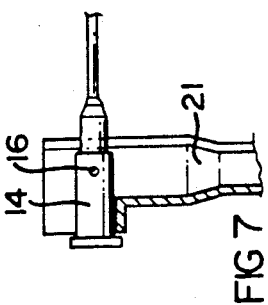

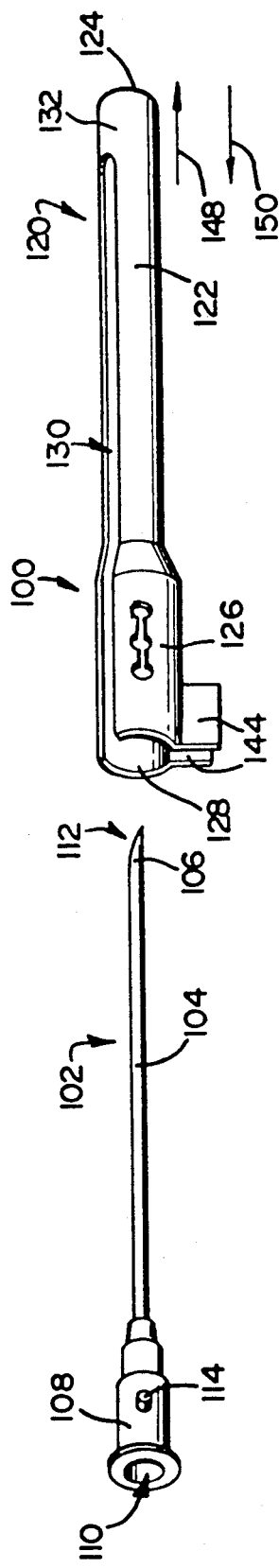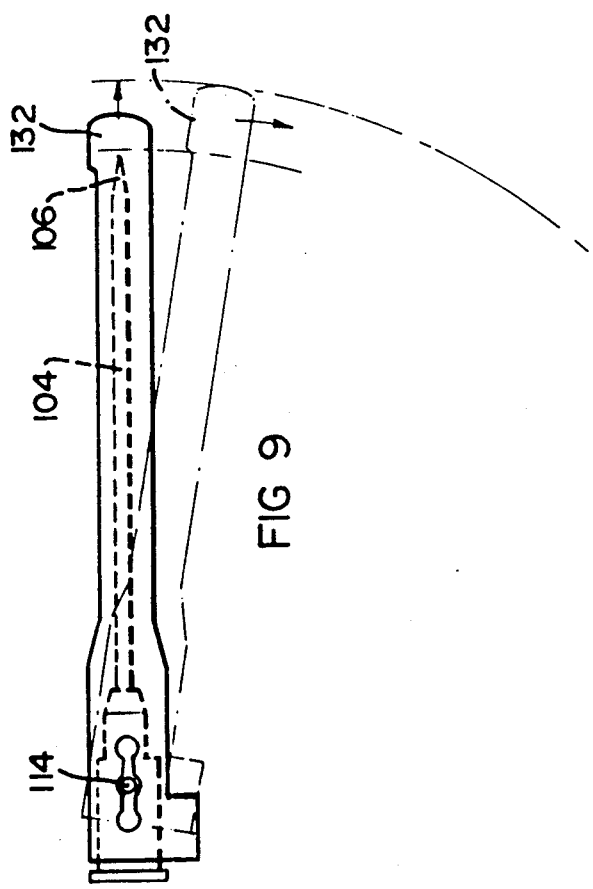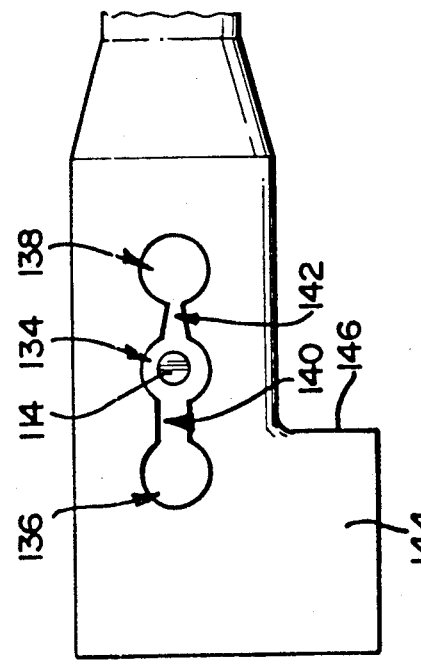

NEEDLE ASSEMBLY

THIS INVENTION relates to a needle assembly.

According to a first aspect of the invention, there is provided a needle assembly, which comprises a needle device comprising a needle base and a hollow needle, having a sharpened or pointed free end, protruding from the base, with a passageway thus extending along the needle, and with an opening to the passageway being provided in proximity to the sharpened end or point of the needle;

a needle guard comprising an elongate protective sheath around the needle such that the sharpened end of the needle is protected by the sheath, an elongate opening extending along the sheath and through which the needle can pass, and a first hinge component in or on the sheath; and a second hinge component in or on the base, with the first and second hinge components co-operating with each other such that the needle guard is pivotal from its position ('the primary position') in which the sharpened needle end or point is protected by the sheath, to a secondary position in which the needle point is exposed for use.

The needle device can thus be a hypodermic needle, catheter needle, cannula, needles used for introduction of intravenous type cannulas, spinal needles, or the like, used for the injection of, or removal of, fluids or gases parenterally or subcutaneously.

The sheath may have a complementary shape to the needle. More particularly, the sheath may be of hollow cylindrical form having a first open end accommodating the needle base and a second closed end in proximity to the needle point. The elongate opening may be in the form of an elongate slot extending from the first end of the sheath to near its second end.

The first hinge component may comprise a pair of openings in the sheath in proximity to its first end, with the openings being aligned with each other and being located on opposite sides of the slot, while the second hinge component may comprise a pair of pivot pins protruding from the needle base, with each pin being pivotally located in one of the openings. Instead of the hinge openings extending through the sheath, protrusions in which the pins are located may be provided in the sheath. Naturally, the pivot pins can instead be provided on the sheath, and the openings or recesses in the needle base, if desired.

The needle assembly may include retaining means for retaining the sheath in its primary position, to prevent accidental pivoting thereof to its secondary position.

In one embodiment of the invention, the retaining means may comprise a displaceable retaining member in or on the sheath. The retaining member may be in the form of a sleeve over, or inside, the second end of the sheath, the sleeve being displaceable from a first position in which it spans a portion of the slot, so that the needle point is thereby held captive in the sheath thus preventing pivoting of the sheath relative to the needle, to a second position in which the slot is uncovered so that the sheath can pivot to its secondary position. The sleeve may be displaceable in a longitudinal direction. The sleeve may also be displaceable to a third position in which it spans the slot to a greater extent than in the first position. The sleeve and sheath may have complementary holding means for holding the sleeve in its first and second positions as well as in a third position in which the sleeve spans greater portion of the slot and thus overlaps the needle point to a greater extent than in its first position. The sleeve may be in the form of a cap.

In another embodiment of the invention, the retaining means may comprise at least one protrusion protruding inwardly from the sheath in proximity to its first end or protruding outwardly from the needle base, and at least one complementary recess in the needle base or the sheath, so that the protrusion nestles in the recess when the sheath is in its primary position, with the protrusion being disengageable from the recess to permit pivoting of the sheath to its secondary position.

The sheath may be displaceable in a longitudinal direction with respect to the needle from a first position in which the needle point is held captive by a portion of the sheath between the distal end of the slot in the sheath end the second end of the sheath, to a second position in which the needle point is aligned with the slot, to permit pivoting of the sheath from its primary to its secondary position. The length of the slot is thus such that when the sheath is in its first position, the needle is held captive by that portion of the sheath between the distal end of the slot and the second end of the sheath, while when it is in its second position, the needle point passes with clearance through the slot. In other words, in moving the sheath from its first to its second position, it is displaced sufficiently in the direction of the sharpened end of the needle so that it is no longer held captive by the needle in its second position.

The assembly may include a pair of secondary openings in the sheath, spaced longitudinally from the other pair of openings ('the primary openings') and also being capable of accommodating the pivot pins in pivotal fashion, with each secondary opening being connected to its associated first opening by means of a first passageway along which the pivot pin can pass and with the secondary openings being spaced further from the first end of the sheath than the primary openings. Thus, to move the sheath from its second to its first position, it is drawn forward in the direction of the sharpened end of the needle so that the pivot pins move from the second openings, along the first passageways, to the first openings. The reverse movement takes place to move the sheath from its second to its first position.

The assembly may also include a pair of tertiary sheath openings for the pivot pins, the tertiary openings being spaced longitudinally from the secondary openings and located further from the first end of the sheath than the secondary openings, with each tertiary opening being connected to its associated secondary opening by means of a second passageway along which the pivot pin can pass.

The width of the first passageways may be substantially constant, while the width of the second passageways may taper down from the secondary apertures to the tertiary apertures so that, when the sheath is displaced towards the needle base, the pivot pins can pass with limited clearance through the tertiary passageways, e.g. by flexing the material of the sheath slightly, and are then held captive in the tertiary openings, preventing re-use of the needle.

The assembly may include an anchoring member attached to the needle base, with the pivot pins mounted to the anchoring member. In one embodiment of the invention, the anchoring member may be in the form of a ring around the needle base. In another embodiment of the invention, the anchoring member may be in the form of a clip gripping the needle base.

According to a second aspect of the invention, there is provided a needle guard for a needle device comprising a needle base and a hollow needle, having a sharpened or pointed free end, protruding from the base, with a passageway thus extending along the needle, and with an opening to the passageway being provided in proximity to the sharpened end or point of the needle, the needle guard comprising an elongate protective sheath adapted to fit around the needle of the needle device such that the sharpened end of the needle is protected by the sheath;

an elongate opening extending along the sheath and through which the needle can pass; and a first hinge component in or on the sheath, and adapted to co-operate with a complementary second hinge component in or on the base of the needle device, such that the needle guard is pivotal, in use, from a primary position in which the sharpened needle end or point is protected by the sheath, to a secondary position in which the needle point is exposed for use.

The needle guard may include an anchoring member attachable to the needle base and on which the second hinge component is located.

The invention will now be described by way of non limiting example with reference to the accompanying diagrammatic drawings in which:

FIG. 1 shows an exploded three dimensional view of a needle assembly in accordance with one embodiment of the invention;

FIG. 2 shows a longitudinal sectional view of the assembly of FIG. 1;

FIG. 3 shows a vertical sectional view of the assembly of FIG. 1 in non-exploded configuration, with the cap in a first position and the sheath in a primary position;

FIGS. 4 and 5 show sectional views corresponding to a portion of FIG. 3, with the cap in second and third positions respectively;

FIG. 6 shows an enlarged view of a portion of FIG. 3;

FIG. 7 shows a vertical sectional view similar to FIG. 3, of part of the assembly of FIG. 1 only, with the sheath in a secondary position;

FIG. 8 shows an exploded three-dimensional view of a needle assembly according to another embodiment of the invention;

FIG. 9 shows a non-exploded side view of the assembly of FIG. 7;

FIG. 10 shows an enlarged view of a portion of FIG. 8;

Figure 11:
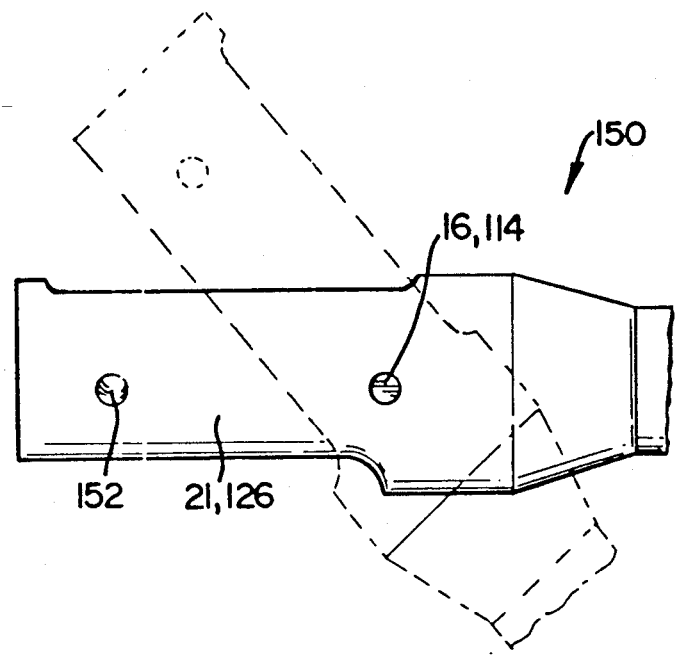
FIG. 11 shows a side view of a portion of a needle assembly according to yet another embodiment of the invention, with the sheath in a primary position.

Referring to FIGS. 1 to 5 of the drawings, reference numeral 10 generally indicates a needle assembly according to one embodiment of the invention.

The assembly 10 comprises a hypodermic needle device, generally indicated by reference numeral 11. The needle device 11 includes a hollow needle 12 having a pointed or sharpened distal end 13, and a needle base or hub 14 from which the needle protrudes. A passageway 15 thus extends through the needle base and along the needle, and terminates in an opening 17 at the sharpened end 13 of the shaft. Pivot pins 16 protrude from opposite sides of the base 14.

The assembly 10 also includes a more-or-less cylindrical sheath or sleeve 20. The circular needle sheath 20 has a wider portion 21 which accommodates the needle base 14 and a narrower portion 22 which accommodates the needle 12. A longitudinal slot 24 extends from an open end 26 of the sheath to a position adjacent a sealed end 28 of the sheath 20. Two apertures 30 are located diametrically opposite one another in the wider portion 21 of the needle sheath. The apertures 30 accommodate the pins so that the sheath can pivot with respect to the needle about an axis extending transversely through the needle base.

The needle sheath 20 includes three parallel circumferential grooves 34, 36 and 38 in proximity to its end 28. The profiles of grooves 34 and 38 are asymmetrical, while that of the groove 36 is symmetrical as indicated in FIG. 6.

The assembly 10 further includes a retaining cap, generally indicated by reference numeral 50, over the distal end of the sheath. The cap 50 comprises a hollow cylindrical body 46 open at one end 48 and sealed at the other end 52. An asymmetrical locating lip or ridge 54 is provided around the inside of the body 46 in proximity to the end 48.

In use, the assembly 10 will be supplied with the cap 50 in the position indicated in FIG. 3 i.e. with the lip 54 engaging the groove 36 so as to maintain the needle point in clean and protected condition. The cap then traps the needle point 13, preventing pivoting of the sheath and keeping the needle sterile i.e. the sheath is held in a primary position. To use the needle 12, the cap is displaced longitudinally relative to the sheath until the lip 54 engages the groove 38, using one hand only. In this position (FIG. 4) the full length of the needle 12 is exposed to the slot 24. The needle 12 is then pivoted outwardly, still using one hand only, from the protective needle sheath 20, through the slot 24, about the pivot pins 16, to a secondary position as indicated in FIG. 7. These operations can thus all be performed using one hand only, so that the other hand of a user is free for performing other acts. The sheath 20 is a relatively loose fit over the needle 12, and the slot width is such that the needle 12 passes freely through it, to permit easy pivoting from the primary to the secondary position, and vice versa.

Once the needle has been used it is pivoted, using one hand only, inwardly back into the needle sheath 20, and the cap 50 is displaced to the position indicated in FIG. 5 in which the lip 54 engages the groove 34. The symmetrical profile of the groove 36 enables the asymmetrical locating lip 54 to be displaced in either direction away from groove 36. However, the asymmetrical profile of the groove 38 engages the asymmetrical lip 54 thereby restraining the cap from being displaced beyond the position of FIG. 4. Similarly, once the cap has been displaced to the position indicated in FIG. 5 the asymmetrical profile of the groove 34 restrains the cap from being displaced again, thereby preventing reuse of the needle.

In this manner the needle end 13 is shielded after the needle 12 has been used, and the needle 12 is prevented from being pivoted outwardly to its secondary position, thereby preventing accidental inoculation or puncture of personnel handling the device after the needle 12 has been used. It is, however, to be appreciated that, if desired, the needle can be re-used by merely displacing the cap sufficiently so that its lip 54 engages the symmetrical groove 36, rather than the asymmetrical groove 34, as shown in FIG. 3. To re-expose the needle point for re-use the cap is then again displaced to the position of FIG. 4.

Accidental puncturing could lead to infection, e.g. with AIDS or hepatitis virusses, of users such as medical personnel by the contaminated, used needle. This is avoided with the sheath 20, as hereinbefore described. Furthermore, as a result of the rigid hinge arrangement comprising the pivot pins 16 and apertures 30 which allows the sheath to move in one dimension or plane only while preventing movement thereof in other dimensions or planes, accurate, smooth and easy pivoting of the sheath relative to the needle is achieved even when using one hand only, with the sheath thus being located accurately and effortlessly over the needle when it is moved to its inoperative position. The sheath is furthermore held captive on the needle base to prevent accidental removal or dislodgement of the sheath from the needle device.

In another embodiment of the invention (not shown), the other end 28 of the sheath 20 can be open, with the cap 50 then protruding into that end of the sheath. The lip 54 will then be provided around the outside of the body 46 of the cap, while the grooves 34, 36 and 38 will be provided on the inside of the sheath 20. In yet a further embodiment of the invention (not shown), the body 46 of the cap can extend over substantially the entire length of the sheath portion 22, with the body 46 then being provided also with an elongate slot similar to the slot 24. The cap can then be rotated relative to the sheath 20 from a position in which the slots are aligned and in which the needle can then be pivoted to its operative position, to a position in which the cap slot is out of register with the slot 24, thereby trapping the needle in the sheath.

Referring to FIGS. 8 to 10 of the drawings, reference numeral 100 generally indicates a needle assembly according to another embodiment of the invention.

The assembly 100 comprises a hypodermic needle device, generally indicated by reference numeral 102. The needle device 102 includes a needle 104 having a pointed or sharpened distal end 106, and a cylindrical base 108 at the other end of the needle 104. A passageway 110 extends through the needle base and along the needle, and terminates in an opening 112 at the sharpened end 106 of the needle. Diametrically opposed pivot pins 114 protrude radially from opposite sides of the needle base 108.

The assembly 100 also includes a more-or-less cylindrical sheath, generally indicated by reference numeral 120. The sheath 120 has a cylindrical portion 122 of more-or-less constant diameter, with the one end 124 of the portion 122 being closed off. The sheath 120 also has a portion 126, the internal diameter of which is somewhat larger than that of the portion 122 and within which the needle base 108 is accommodated snugly. The end 128 of the portion 126 is open. A longitudinally extending slot 130 extends along the portions 126, 122 and terminates some distance from the end 124 of the sheath so that the sheath portion 122 includes a portion 132, in proximity to the sheath end 124, which is unbroken circumferentially.

In the portion 126 of the sheath 120 are provided diametrically opposed pairs of apertures 134, 136 and 138. The apertures 136 are spaced longitudinally from the apertures 134, towards the end 128 of the sheath, while the apertures 138 are spaced longitudinally from the apertures 134, in the direction of the closed end 124 of the sheath. Each aperture 136 is connected to its associated aperture 134 by means of a constant-width passageway 140, while each aperture 138 is connected to its associated aperture 134 by means of a passageway 142. The width of the passageway 142 tapers down from the aperture 134 to the aperture 138.

One of the pivot pins 114 can be accommodated pivotally in one of the apertures 134, 136 and 138, while the width of the passegeway 140 is sufficient for the pivot pin 114 to pass slidingly therethrough. However, the width of the passageway 142, at its narrowest, is such that the pivot pin cannot readily pass therethrough and some force must be used to effect this, with the passage of the pivot pin 114 along the passageway 142 only being possible as a result of some flexing, albeit of a minute scale, of the material of the sheath.

The sheath 120 is of plastics material such as polyethylene or polypropylene.

A pair of spaced cheek plates 144 protrude outwardly from the end 128 of the sheath and the cheek plates are connected together by means of a arcuate bridging portion 146.

In use, the assembly 100 is supplied with the sheath 120 located in a primary inoperative position as indicated in FIG. 9, i.e. with the pivot pins 114 located in the apertures 134 and the needle point 106 being held captive by the portion 132 of the sheath. When it is desired to use the needle 104, the sheath 120, while it is still in its inoperative position as indicated in FIG. 2, is moved forwardly, using one hand only, in the direction of arrow 148, with the pivot pins 114 sliding along the passageways 140, until the pivot pins nestle in the apertures 136. The sheath 120 can then be pivoted, using one hand only, to a secondary or operative position, as indicated in broken line in FIG. 2, in which the needle point 106 is exposed. The cheek plates 144 and the bridging portion 146, which engage the needle base 108, or a portion of the syringe (not shown) to which the needle is fitted, serve to limit the degree to which the sheath can be pivoted about the pivot pins 114.

After use, the sheath can then be pivoted back into its inoperative position as indicated in full lines in FIG. 2 whereafter it can be displaced in the direction of arrow 150 so that the pivot pins 114 again move along the passageways 140 into the aperture 134 and from there along the passageways 142, under some force, into the apertures 138. These operations can all be performed using one hand only. The pivot pins 114 will thus be held captive in the apertures 138, preventing re-use of the needle 102. The needle point 106 will then nestle within the portion 132 of the sheath in which it is protected so that it cannot accidentally prick, and infect, a handler.

Figure 12:
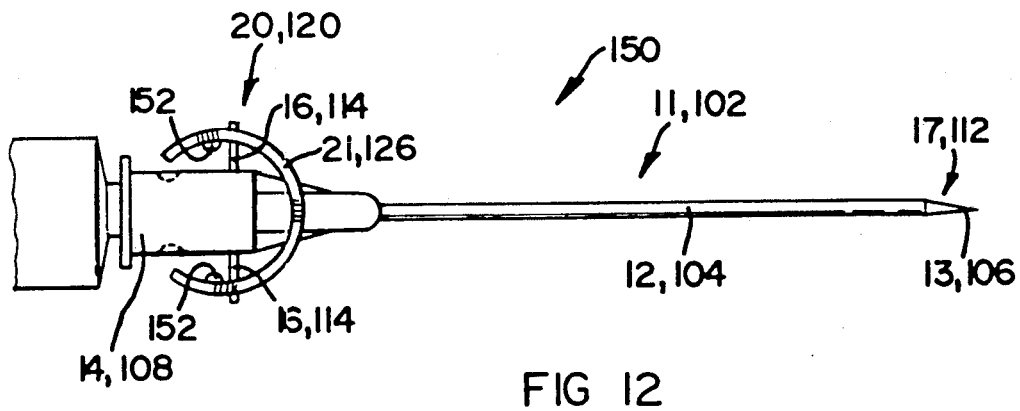
FIG. 12 shows a plan view of the assembly of FIG. 11, with the sheath in a secondary position.

Referring to FIGS. 11 and 12, reference numeral 150 generally indicates a needle assembly, according to yet another embodiment of the invention.

Parts of the assembly 150 which are the same or similar to those of the assemblies 10, 100 are indicated with the same reference numerals.

In the assembly 150, the sheath slot 24, 130 stops short of the portion 21, 126 of the protective sheath, while a pair of gripping knobs or protrusions 152 protrude inwardly from the sheath portion 21, 126.

When the sheath is in its primary position as indicated in full line in FIG. 11, the knobs 152 engage recesses 154 in the needle base 14, 108, thereby to restrain the sheath against free pivoting to its secondary position as indicated in FIG. 11. However, by exerting sufficient force (using one hand only) on the sheath 11, 102, the knobs or protrusions can naturally be disengaged from the recesses 154 to permit such pivoting.

Figure 13:
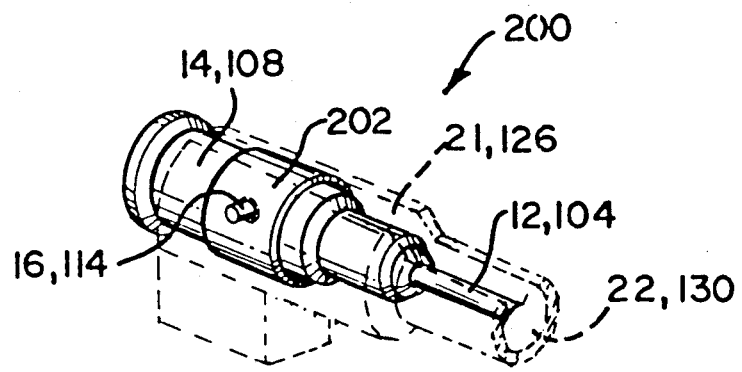
FIGS. 13 and 14 show three dimensional views of parts of needle assemblies according to still further embodiments of the invention.

Referring to FIG. 13, reference numeral 200 generally indicates a needle assembly according to yet another embodiment of the invention.

Parts of the assembly 200 which are the same or similar to those of the needle assemblies hereinbefore described, are indicated with the same reference numerals.

The assembly 200 includes a ring 202 of plastics material, which fits around the needle base 14, 108, with the pivot pins 16, 114 protruding from the ring 202 rather than from the needle base. The ring can grip the needle base frictionally or it can be fixed thereto, e.g. by means of an adhesive.

Figure 14:
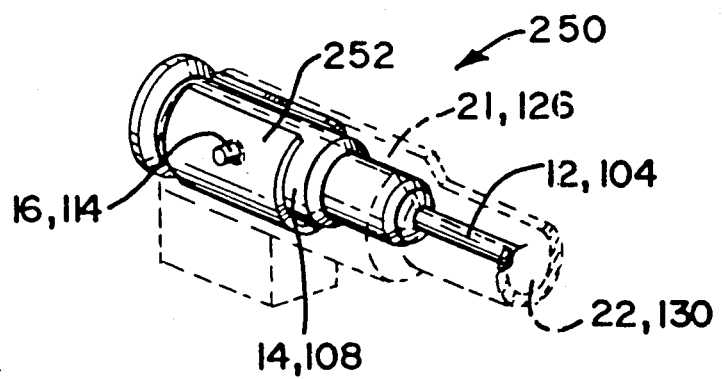

Referring to FIG. 14, reference numeral 250 generally indicates a needle assembly according to a still further embodiment of the invention.

Parts of the assembly 250 which are the same or similar to those of the needle assemblies hereinbefore described, are indicated with the same reference numerals.

The assembly 250 includes a clip 252 which grips the needle base 14, 108 frictionally, with pivot pins protruding from the clip 252 rather than from the needle base. The clip 252 is more-or-less horseshoe-shaped in cross-section.

Needle guards in accordance with the invention and incorporating the ring 202 or clip 252 can thus be used on existing needle devices, to provide the protection as hereinbefore described.

I claim:

1. A needle assembly, which comprises
   a needle device comprising a needle base and a hollow needle, having a pointed free end, protruding from the base, with a passageway extending along the needle, and with an opening to the passageway being provided in proximity to the pointed end of the needle;
   a needle guard comprising a hollow cylindrical sheath around the needle and having a first open end accommodating the needle base and a second closed end in proximity to the needle point, an elongate slot extending from the first end of the sheath to near its second end and through which the needle can pass, and a first pair of openings in the sheath in proximity to its first end, with the openings being aligned with each other and being located on opposite slides of the slot;
   a pair of complementary pivot pins protruding from the needle base, with each pin being pivotally located in one of the openings such that the needle guard can be pivoted from a primary position in which the pointed end is protected by the sheath, to a secondary position in which the needle point is exposed for use; and
   a pair of secondary openings in the sheath, spaced longitudinally from the first pair of openings and also being capable of accommodating the pivot pins in pivotal fashion, with each secondary open being connected to its associated first opening by means of a first passageway along which the pivot pin can pass and with the secondary openings being spaced further from the first end of the sheath than the first pair of openings so that the sheath is displaceable in a longitudinal direction with respect to the needle from a first position in which the needle point is held captive by a portion of the sheath between the distal end of the slot in the sheath and the second end of the sheath, to a second position in which the needle point is aligned with the slot, to permit pivoting of the sheath from its primary to its secondary position.

2. A needle assembly according to claim 1, which includes a pair of tertiary sheath openings for the pivot pins, the tertiary openings being spaced longitudinally from the secondary openings and located further from the first end of the sheath than the secondary openings, with each tertiary opening being connected to its associated secondary opening by means of a second passageway along which the pivot pin can pass.

3. A needle assembly according to claim 2, wherein the width of the first passageways is substantially constant while the width of the second passageways tapers down from the secondary openings to the tertiary openings so that, when the sheath is displaced towards the needle base, the pivot pins can pass with limited clearance through the tertiary passageways and are then held captive in the tertiary openings, preventing re-use of the needle.

4. A needle assembly, which comprises
   a needle device comprising a needle base and a hollow needle, having a pointed free end, protruding from the base, with a passageway extending along the needle, and with an opening to the passageway being provided in proximity to the pointed end of the needle;
   a needle guard comprising a hollow cylindrical sheath around the needle and having a first open end accommodating the needle base and a second closed end in proximity to the needle point, an elongate slot extending from the first end of the sheath to near its second end and through which the needle can pass, and a first pair of openings in the sheath in proximity to its first end, with the openings being aligned with each other and being located on opposite sides of the slot;
   an anchoring member attached to the needle base;
   a pair of complementary pivot pins protruding from the anchoring member, with each pin being pivotally located in one of the openings such that the needle guard can be pivoted from a primary position in which the pointed end is protected by the sheath, to a secondary position in which the needle point is exposed for use; and
   a pair of secondary openings in the sheath, spaced longitudinally from the first pair of openings and also being capable of accommodating the pivot pins in pivotal fashion, with each secondary opening being connected to its associated first opening by means of a first passageway along which the pivot pin can pass and with the secondary opening being spaced further from the first end of the sheath than the first pair of openings so that the sheath is displaceable in a longitudinal direction with respect to the needle from a first position in which the needle point is held captive by a portion of the sheath between the distal end of the slot in the sheath and the second end of the sheath, to a second position in which the needle point is aligned with the slot, to permit pivoting of the sheath from its primary to its secondary position.

5. A needle assembly according to claim 4, wherein the anchoring member is in the form of a ring around the needle base.

6. A needle assembly according to claim 4, which includes a pair of tertiary sheath openings for the pivot pins, the tertiary openings being spaced longitudinally from the secondary openings and located further from the first end of the sheath than the secondary openings, with each tertiary opening being connected to its associated secondary opening by means of a second passageway along which the pivot pin can pass.

7. A needle assembly according to claim 6, wherein the width of the first passageways is substantially constant while the width of the second passageways tapers down from the secondary openings to the tertiary openings so that, when the sheath is displaced towards the needle base, the pivot pins can pass with limited clearance through the tertiary passageways and are then held captive in the tertiary openings, preventing re-use of the needle.

* * * * *